United States Patent [19]

Cuny et al.

[11] 4,352,931
[45] Oct. 5, 1982

[54] LIN-BENZOAMINOPURINOLS

[75] Inventors: Eckehard K. T. Cuny, Seeheim; Frieder W. Lichtenthaler, Mühetal; Alfred R. Moser, Kassel, all of Fed. Rep. of Germany

[73] Assignee: Siegfried Aktiengesellschaft, Zofingen, Switzerland

[21] Appl. No.: 152,527

[22] Filed: May 22, 1980

[51] Int. Cl.³ .......................................... C07D 487/04
[52] U.S. Cl. ................................................... 544/251
[58] Field of Search .......................................... 544/251

[56] References Cited

U.S. PATENT DOCUMENTS

| | | | |
|---|---|---|---|
| 2,868,803 | 1/1959 | Druey et al. | 544/262 |
| 3,519,716 | 7/1970 | Hitchings et al. | 544/262 |
| 3,624,205 | 11/1971 | Hitchings et al. | 424/251 |
| 3,626,064 | 12/1971 | Hitchings et al. | 424/251 |
| 4,223,143 | 9/1980 | Cuny et al. | 544/251 |

*Primary Examiner*—Paul M. Coughlan, Jr.
*Attorney, Agent, or Firm*—Werner W. Kleeman

[57] ABSTRACT

Novel benzologs or pyrazolo-quinazoline derivatives of the formula (I)

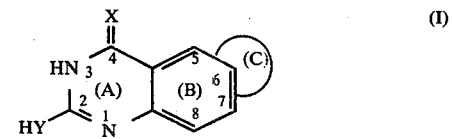

wherein X and Y are independently selected from oxygen, sulphur and imino and wherein ring (C) is a pyrazole ring fused to ring (B) via one of the three ortho positions or sides of ring (B); the fused pyrazole ring (C) is either in the 4,3- or the 3,4-arrangement; and tautomers of formula (I) compounds; when X is not oxygen, i.e. stands for sulphur or imino, Y may stand for a covalent bond that links the hydrogen directly to the carbon atom in position 2.

Two methods for producing the novel formula (I) compounds are disclosed. The first or indazole method starts from a precursor having a benzene moiety (ring B) and a pyrazolo moiety (ring C) fused therewith, i.e. the indazole structure; ring (B) carries two vicinal substituents for forming the pyrimidine moiety or ring (A) by cyclization. The second or quinazoline method starts from a precursor having the pyrimidine moiety (A) and the benzene moiety (B) fused therewith, i.e. the quinazoline structure, and carrying two vicinal substituents for forming the pyrazole moiety (C) by cyclization.

The first method, in addition to yielding the novel benzologs, provides for improved synthesis of previously disclosed benzo-allopurinols.

Novel compounds of formula (I) are benzologs of such well known and biologically active compounds as oxipurinol, aminopurinol and thiopurinol and are expected to be applicable for comparable pharmaceutical purposes.

1 Claim, No Drawings

LIN-BENZOAMINOPURINOLS

CROSS-REFERENCE TO RELATED CASES

This application is related to subject matter disclosed in our commonly assigned U.S. application Ser. No. 968,577 filed Dec. 11, 1978 now U.S. Pat. No. 4,223,143 and in the divisional therefrom filed on Apr. 14, 1980 as Ser. No. 140,307, now abandoned.

BACKGROUND OF THE INVENTION

1. Field of the Invention

The present invention relates to novel benzologs and to methods of producing benzologs.

2. Description of the Prior Art

Purinol-type compounds of the formula (V)

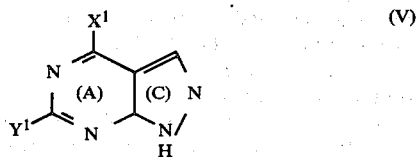

wherein $X^1$ and $Y^1$ stand for hydroxy, mercapto, amino or hydrogen are known in the art; they are known to have biological activities and many of them are used in pharmacology. For example, the compound (A) wherein $X^1$ is hydroxy and $Y^1$ is hydrogen is the pyrazolo[3,4-d]pyrimidine-4-one known under the generic name Allopurinol. Since its first preparation more than two decades ago (cf. R. K. Robbins, J. Am. Chem. Soc. 78 (1956) 784) it has been used for therapeutical purposes as an inhibitor of xanthine oxidase and for its controlling effect upon the concentration of uric acid in human blood, e.g. for treatment of gout.

Allopurinol and related compounds of formula (V) as well as therapeutical uses of such compounds are disclosed, for example, in U.S. Pat. Nos. 3,624,205, 2,519,716 and 3,626,064 and in British Pat. No. 975,850. Typical related compounds are oxipurinol (formula V: both $X^1$ and $Y^1$ are hydroxy), aminopurinol (formula V: $X^1$ is hydroxy, $Y^1$ is amino), thiopurinol (formula V: $X^1$ is mercapto, $Y^1$ is hydrogen) and the like. In addition to, or instead of, xanthine oxidase inhibiting effect, such compounds of formula (V) have, or are believed to have, important antineoplastic and immunosuppressive effects and have, or may have, important clinical uses including therapy of cancer, e.g. human leukemia.

As set forth in our above mentioned U.S. application Ser. No. 968,577 now U.S. Pat. No. 4,223,143 Allopurinol has a relatively low solubility and must be used at a relatively high dosage level and it is believed that similar considerations would apply to the prior art compounds of formula (V) as a class. Accordingly, there is a need to find new compounds having a sufficient structural similarity with the formula (V) compounds to retain or increase their beneficial effects and/or to provide such formula (V)-related substances that have generally more favorable physiological and therapeutic effects than the formula (V) compounds proper.

Accordingly, it is a main object of this invention to provide for novel compounds that include the effective moieties of the formula (V) compounds in a modified structural arrangement.

A further object is to provide for purinol-related compounds for therapeutic use instead of, or in combination with, purinols.

Another object is a method of producing novel benzologs of formula (V) compounds as well as improved synthesis of previously disclosed benzologs.

Other objects will become apparent as the specification proceeds.

SUMMARY OF THE INVENTION

According to the present invention we have found a group of novel purinol benzologs of the formula (I)

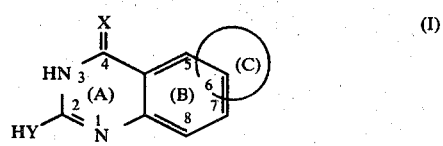

wherein X and Y are each selected from the group consisting of oxygen (O), sulphur (S) and imino (NH); alternatively, Y may stand for a single bond thus connecting the hydrogen of HY- directly with the carbon atom in position 2 of formula (I); provided, however, that X is not oxygen when Y is a single bond.

Ring (C) of formula (I) is a pyrazole ring fused to ring (B) via one ortho position thereof. The term "fused ring (B) via one ortho position thereof" is used here to indicate that ring (C) can be fused to ring (B) in any pair of vicinal positions 5/6, 6/7 and 7/8 thereof.

As will be understood, ring (B) forms a quinazoline structure with ring (A) and the above mentioned vicinal positions of ring (B) are the f, g and h sides of the quinazoline formula

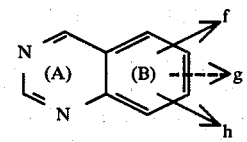

Thus, when referring to the f-, g- and h-sides of ring (B), this is to be understood as relating to ring (B) as a part of fused moiety of the quinazoline structure.

GENERAL DISCUSSION OF PREFERRED EMBODIMENTS

Accordingly, the invention includes both the linear and the angular benzolog structures

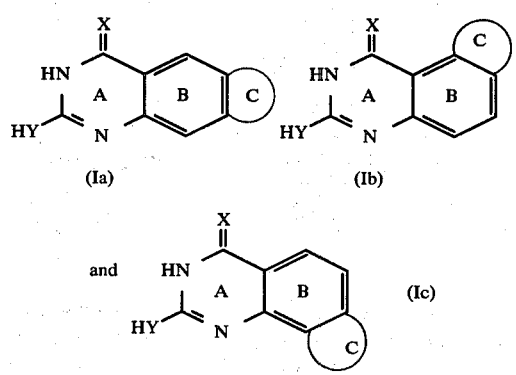

i.e. fusion of C at the f, g or h side.

In general, linear structures of formula (Ia) and proximal angular structures (Ib) may be preferable, i.e. g-side and f-side fusion of ring (C), respectively.

Linear structures (Ia) with g-side fusion of (C) are particularly preferred since their molecular geometry—as compared to that of the conventional purinols of formula (V)—is lengthened but in one direction by about 2.4 Å, whilst in the angular purinols (Ib) and (Ic) the pyrimidine and pyrazole structural features of purinol are extended via a kink, i.e. in a somewhat more complex manner.

In both the angular and the linear compounds according to the invention the insertion of the benzene ring into the conventional purinol structure (V) retains the enzyme-bonding sites of the terminal rings and increases the potential for H-interactions.

Further, the fused pyrazole ring (C) of formula (I) may be either in a 4,3- or 3,4-arrangement, i.e.

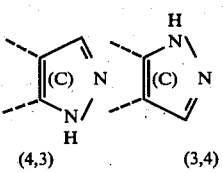

relative to the quinazoline moiety of formula (I); also, the invention includes tautomeric forms due to interchange of the hydrogen atom on the nitrogen atoms in the pyrazole moiety (C) in either the above 4,3- or 3,4-arrangement.

The invention further includes the tautomers of formula (I) compounds, both as regards the structures (IA), (Ib), (Ic), and the pyrazole arrangement.

Tautomeric forms of the formula (I) compounds may involve either or both X and Y as either or both may be connected to ring (A) via a double bond (in which case the adjacent nitrogen carries a hydrogen atom) or via a single bond (in which case the hydrogen from the adjacent nitrogen "migrates" to X and/or Y); these oxo/enol, imino/enamine and thio/enthiol tautomers thus comprise the structures (Id), (Ie), (If), (Ig):

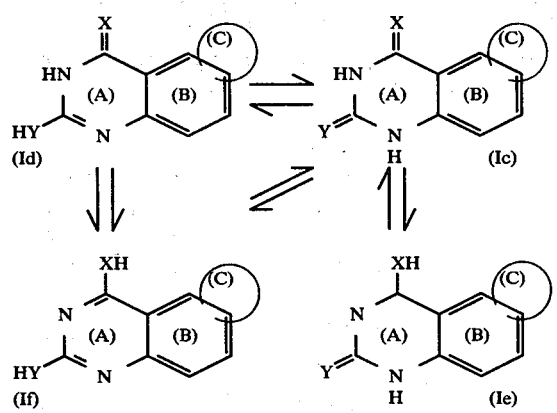

As indicated above, Y can be a direct bond when X is either sulphur or imino (i.e. not oxygen); these novel benzologs according to the invention can be represented by formula (II)

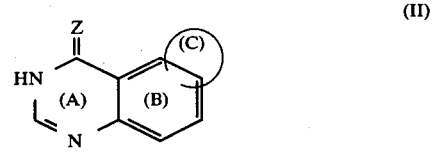

wherein Z is sulphur or imino while ring (C) is defined as above. Again, formula (II) is intended to encompass the tautomeric imino/enamine and thio/enthioltautomers with regard to Z in partial analogy with X as explained above as well as the pyrazole arrangements 4,3 and 3,4 and tautomers thereof.

Generally, compounds of formula (I) could be obtained from two types of precursors; one type of suitable precursor is a preformed indazole-type compound having vicinal substituents on its benzene moiety for forming the fused pyrimidine moiety (A) by direct cyclization or by reaction with a second reactant required for any complemental members of ring (A) that are not on the indazole precursor.

Synthesis with either type of indazole precursors will be called "indazole routes" herein. For example, a suitable indazole precursor has the structure of formula (III-1)

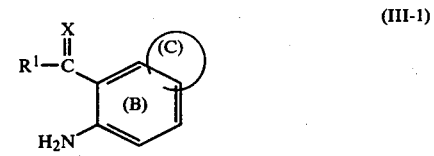

wherein X is defined as above and $R^1$ is an amino-reactive first leaving group, e.g. hydroxyl, lower alkoxy, amino or halogen, and ring (C) is as defined above. A suitable second reactant for forming pyrimidine ring (A) is an amino compound of either formula

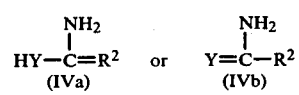

wherein Y is oxygen, sulphur or imino and $R^2$ is a second amino-reactive leaving group of the same type as $R^1$ or of a comparable bivalent type, such as oxygen. For example, $R^1$ in formula (III-1) can be hydroxyl thus being capable of condensation with one hydrogen of the amino in (IVa) or (IVb); when $R^2$ is oxygen, for example, this is an amino-reactive group capable of condensation with both hydrogens of the amino group of the indazole of formula (III-1); another example of an amino-reactive leaving group $R^1$ and/or $R^2$ is the amino group proper as it is capable of condensation (via $NH_3$ elimination) with the amino group in either of the formulae (III-1), (IVa) and (IVb).

Thus, typical and preferred examples of suitable second reactants in the above indazole route are urea, formamide and guanidino carbonate.

As will be apparent, the indazoleroute may yield both the novel benzologs of formula (I) or (II) as well as the benzo allopurinols disclosed in our above mentioned U.S. applications. As production of the benzo allopurinols via the indazole route using formula (III-1) compounds and formamide as second reactant has been disclosed, this synthesis is part of the present invention only insofar as Y in formula (IVa) is not just a bond when X is oxygen.

Another synthesis route to the compounds of formula (I) and (II) is via a precursor of the quinazoline type and is called "quinazoline route" herein. The precursor includes the preformed pyrimidine ring (A) while pyrazole ring (C) is formed by reaction of the precursor.

Thus, the quinazoline precursor has the formula (III-2)

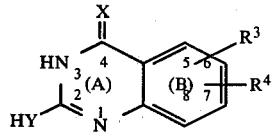

wherein X and Y are as defined above and $R^3$ and $R^4$ are vicinal substituents in positions 5/6, 6/7 and 7/8 of ring (B); $R^3$ and $R^4$ are substituents capable of forming said pyrazole ring (C) by cyclization in a manner generally known from purinol syntheses.

A third synthesis route to obtaining the formula (I) and notably formula (II) compounds involves transformation of X; for example, an oxygen as X in formula (I) or (II) can be transformed into sulphur by adapting prior art procedures, e.g. of the type described by J. A. Montgomery et al in J. Org. Chem. 28 (1963) 2304.

For pharmaceutical use inventive compounds of formulae (I) and (II) can be used in a manner generally similar to that known for prior art purinols of formula (V) to complement or replace the formula (V) compounds and in similar dosages as well as in similar pharmaceutical compositions, i.e. admixed, dissolved, dispersed or otherwise distributed in a pharmacologically acceptable solid, liquid or semi-solid carrier. Such compositions may also include other active ingredients, e.g. the corresponding formula (V) purinols.

Examples of preferred specific compounds of the invention are compounds of formula (I) wherein both X and Y are oxygen; these compounds will be called benzo-oxipurinols herein.

Also preferred are compounds of formula (I) wherein X is oxygen and Y is imino; these compounds will be called benzo-aminopurinols herein.

Particularly preferred sulphur-containing compounds according to the invention are those of formula (II) wherein X is sulphur; these compounds will be called benzo thiopurinols herein.

Precursor compounds for the indazole route and the quinazoline route can be obtained, for example, in the general manner disclosed in our above mentioned U.S. applications, making suitable modifications as required in view of the nature of X and Y in formulae (I) and (II) of the present invention.

For example, in the synthesis of the novel benzooxipurinol and benzo-aminopurinol via the indazole route a suitable and preferred precursor is the indazole of formula (5)

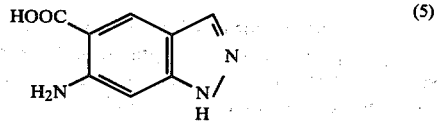

This precursor compound is disclosed in example XIII of our U.S. application Ser. No. 968,577 now U.S. Pat. 4,223,143 and can be used for the purposes of the present invention.

However, other ways to suitable precursor compounds are feasible and a preferred alternative route to the indazole of formula (5) will be illustrated in the following reaction scheme:

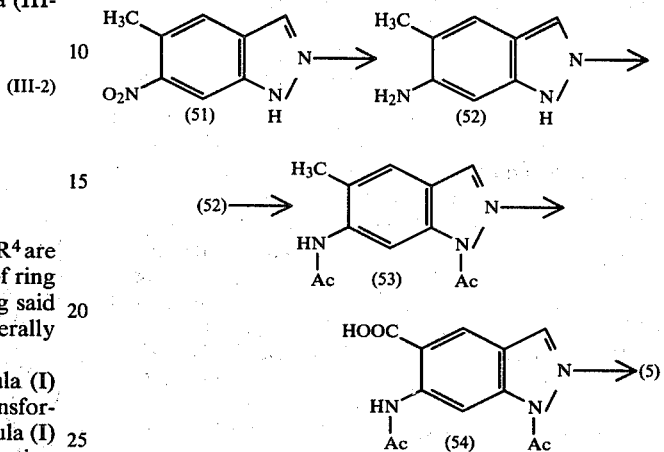

(Ac stands for acyl, preferably acetyl).

The overall yield of (5) in this method is about 40% and thus substantially better than that of the method disclosed in our above mentioned U.S. application.

As the precursor (5) can be used for the indazole route both in the preparation of the subject novel benzologs as well as in the preparation of the benzo allopurinols disclosed in our previous U.S. application, the above reported synthesis of (5) is an advance even for synthesis of the benzo allopurinols.

Yet a further method for obtaining suitable precursors has been described by R. H. Foster and N. J. Leonard in J. Org. Chem. 44 (1979), pages 4609–4611, in their publication about synthesis of lin-benzo-allopurinol.

Specific examples embodying the invention are set forth below. These examples are illustrative and not to be understood as limiting the scope and underlying principles of the invention in any way. In the examples, temperatures are in degree (°) Centigrade, percentages are by weight. Melting points (m.p.) were determined on a Bock Monoskop and are uncorrected. NMR, IR and mass spectra were taken to ascertain the structures. Results of elemental analysis are in percent by weight. The NMR spectra were obtained on a "Varian A60" and "XL-100" spectrometer using TMS (tetramethyl silane) as an internal standard; chemical shifts are expressed as parts per Million ($\delta$) from TMS. IR spectra were determined in pressed disks of potassium bromide using a "Beckman 125" spectrophotometer. The mass spectra were obtained on a "Varian CH 34" and "MAT 311A" spectrometer. Thin layer chromatography was run on silicagel/plastic plates ("Kieselgel $F_{254}$") and column chromatography was done on silicagel ("Kieselgel 60", Merck, Darmstadt, West-Germany).

EXAMPLE I

6-Amino-5-methylindazole (formula 52)

8 g (45.2 mmol) of 5-methyl-6-nitro-indazole (formula 51), obtained according to E. Noelting, Ber. Dtsch. Chem. Ges. 37 (1904) 2556, are dissolved in 640 ml of 50% aqueous ethanol. A mixture of 80 g of ferrous sulphate in 400 ml of water and 80 ml of aqueous ammonia were added. The reaction mixture was refluxed for 20 hours and filtered while still hot. Removal of the ethanol and purification of the precipitated product with charcoal yielded 4.80 g (72%) of the target compound, m.p. 241°-242° C.

Substantial purification of (52) is not required when used for synthesis of (53) as set forth below.

EXAMPLE II

1-Acetyl-6-acetamido-5-methyl-indazole (formula 53)

6.0 g (40.8 mmol) of the compound (52) obtained in example I are dissolved in a mixture of 80 ml of acetic acid and 160 ml of acetic anhydride by heating and the solution was allowed to stand over night.

The target product (53) precipitates during that period in the form of colorless needless. The mother liquor yields a further amount of (53) by evaporation in vacuo (up to 0.1 Torr) and recrystallization of the residue from ethanol. Total yield is 8.48 g (90%), m.p. 243°-245° C.

MS (70 eV): m/e=231 (12%, M+), 189 (1%, M+—OAc), 147 (5%, M+—2.OAc), 43 (100%, CH$_3$CO+)

$C_{12}H_{13}N_3O_2$ calculated: C 62.32, H 5.67, N 18.17, found: C 62.29, H 5.60, N 18.05.

EXAMPLE III

1-Acetyl-6-acetamido-indazole-5-carboxylic acid (formula 54)

1 g (4.32 mmol) of the compound (53) obtained in example II is dissolved in 200 ml of t-butanol while heating. 100 ml of water are added and the mixture is heated to reflux temperature. During a period of 6 hours, a total of 3.5 g of KMnO$_4$ is added in portions. The solution obtained after termination of the reaction is filtered while still hot and the butanol is removed by evaporation. The alcaline solution obtained is adjusted to pH 3-4 by addition of 2 N HCl. The target product (54) precipitates and 0.65 g (65%) of this colorless product are obtained; it sublimates at temperatures above 215° C. yielding fine crystalline needles (decomp. at 300° C. without melting).

MS (70 eV): m/e=261 (5%, M+), 219 (19%, M+—OAc), 177 (21%, M+—2.OAc), 159 (52%, 177—H$_2$O), 132 (21%, 159—CO), 43 (100%, CH$_3$CO+).

$C_{12}H_{11}N_3O_4$ calculated: C 55.17, H 4.24, N 16.09, found: C 55.08, H 4.20, N 16.10.

EXAMPLE IV

6-Amino-1H-indazole-5-carboxylic acid (formula 5)

1.5 g (5.75 mmol) of the compound of formula (54) obtained in example III are suspended in 6 N HCl and evaporated to dryness on a water bath. The procedure is repeated until a reddish-brown powder is obtained that is mixed with water to produce a solution. The pH of this solution is adjusted to 6.5 with 10% aqueous sodium hydroxide.

An ochre-colored pulverulent substance is obtained and separated. This is the target acid (5) and is obtained in quantitative yield. The product sublimates beginning at 260° C. in the form of fine yellow needles which melt at 281° C.

MS (70 eV): m/e=177 (79%, M+), 160 (14%, M+—OH), 159 (100%, M+—H$_2$O), 132 (74%, 159—CO).

$C_8H_7N_3O_2$ calculated: C 54.23, H 3.98, N 23.72, found: C 54.21, H 3.87, N 23.59.

EXAMPLE V

1H-Pyrazolo[4,3-g]-quinazoline-5,7-dione (formula 10, "lin-benzooxipurinol")

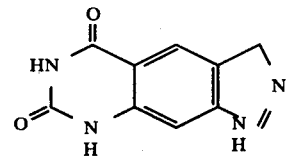

700 mg (4 mmol) of the precursor compound (5) obtained in example IV are mixed with 2.1 g of urea and the mixture is ground in a mortar. The ground mixture is heated for 2 hours on an oil bath at 160° C. The mixture melts and ammonia is developed as a by-product of condensation. The target product (10) is obtained in a yield of 0.44 g (55), m.p. >330° C.

MS (70 eV): m/e=202 (49%, M+), 159 (50%, M+—CONH), 132 (41%, 159—CO).

$C_9H_6N_4O_2$ calculated: C 53.46, H 2.99, N 27.72, found: C 53.47, H 2.88, N 27.66.

EXAMPLE VI

7-Amino-1H-pyrazolo[4,3-g]-quinazoline-5(6 H)-one (formula 20, "lin-benzo aminopurinol")

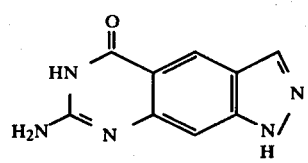

0.6 g (3.39 mmol) of the precursor acid (5) obtained as in example IV are mixed with 0.6 g of guanidino carbonate and finely ground in a mortar. The ground mixture is heated for a period of 2 hours on an oil bath at 185° C. A melt is formed and ammonia is developped. The mixture is allowed to cool and is taken up in water and filtered. The target product (20) is obtained in an amount of 0.42 g (62%), m.p. >330° C.

M+-peak (70 eV) at m/e=201.

$C_9H_7N_5O$ calculated: C 53.73, H 3.51, N 34.84, found: C 52.94, H 3.48, N 34.77.

EXAMPLE VII

Pyrazolo[4,3-g]-quinazoline-5-thiol (formula 30, "lin-benzo thiopurinol")

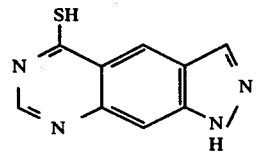

This is an example of producing the subject benzologs by conversion of preformed benzologs. The starting compound is the lin-benzo-allopurinol or pyrazolo[4,3-g]-quinazoline-5(6H)-one as described in Example XIV of our U.S. application Ser. No. 968,577.

A suspension of 0.93 g of the lin-benzo-allopurinol and 4.5 g of phosphor pentasulfide (P$_2$S$_5$) in dry pyridine (150 ml) are refluxed with stirring for a period of 4 hours. After standing over night at room temperature the mixture is evaporated to dryness and the residue is triturated with hot water (150–200 ml), whereafter crystalline target compound (30) is removed by filtration: 0.86 g (85%); m.p. >330° C.

MS (EI): m/e=202 (M+, 100%), 169 (62%, M—SH). UV (phosphate buffer, pH 7.5): $\lambda_{max}$=246.4, 297.5, 301.6 and 372, shoulders at 226, 362, 388, 393 nm.

$C_9H_6N_4S$ calculated: C 53.45, H 2.99, N 27.70, S 15.85, found: C 53.31, H 2.95, N 27.66, S 15.69.

Various modifications of the above disclosed specific embodiments of the invention will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. A compound having the formula (20)

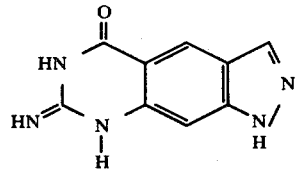

and tautomers thereof.

* * * * *